United States Patent [19]

N'Guyen et al.

[11] Patent Number: 5,352,695
[45] Date of Patent: Oct. 4, 1994

[54] USE OF LYSINE PYRROLIDONE CARBOXYLATE AND/OR OF ARGININE PYRROLIDONE CARBOXYLATE AS AN ANTOXIDANT SUBSTANCE IN COSMETIC OR PHARMACEUTICAL COMPOSITIONS

[75] Inventors: Lan Quang N'Guyen, Antony; Etienne Soudant, Fresnes, both of France

[73] Assignee: L'Oreal, Paris, France

[21] Appl. No.: 873,138

[22] Filed: Apr. 24, 1992

[30] Foreign Application Priority Data

Apr. 24, 1991 [FR] France ................. 91 05062

[51] Int. Cl.$^5$ ................. A61K 31/40; A61K 31/195
[52] U.S. Cl. ................. 514/423; 514/458; 514/564; 514/565; 514/844
[58] Field of Search ............. 514/844, 458, 423, 424, 514/564, 565

[56] References Cited

U.S. PATENT DOCUMENTS 4,839,387 6/1989 Poli ........................ 514/19
4,981,845 1/1991 Pereira ..................... 514/557

OTHER PUBLICATIONS

Takeshi Yanagida, Patent Abstracts of Japan, vol. 10, No. 182, Jun. 25, 1986, C-356, 2238, entitled "Dermal External Drug".

M. Desrame et al., "L'acide pyrrolidone carboxylique et ses dérivés dans l'industrie comsétique", Parfums, Cosmetiques, Aromes, No. 93, Jun.–Jul. 1990, pp. 93-99.

Katsura Shimizu, Patent Abstracts of Japan, vol. 5, No. 136, Aug. 28, 1981, C-69, 808, entitled "Cosmetics".

Ahmad et al., The Antioxidant Activity of Amino Acids in Two Vegetable Oils, JAOCS. vol. 60(4) (1983) pp. 837-840.

*Primary Examiner*—Marianne M. Cintins
*Assistant Examiner*—Phyllis G. Spivack
*Attorney, Agent, or Firm*—Wegner, Cantor, Mueller & Player

[57] ABSTRACT

The use of lysine pyrrolidone carboxylate and arginine pyrrolidone carboxylate are disclosed as antioxidants in a cosmetic composition combined with at least one phenolic derivative.

8 Claims, No Drawings

USE OF LYSINE PYRROLIDONE CARBOXYLATE AND/OR OF ARGININE PYRROLIDONE CARBOXYLATE AS AN ANTOXIDANT SUBSTANCE IN COSMETIC OR PHARMACEUTICAL COMPOSITIONS

The present invention concerns the use of lysine pyrrolidone carboxylate (designated below as lysine pidolate) and/or of arginine pyrrolidone carboxylate (hereinafter called arginine pidolate) as an antioxidant substance in the preparation of cosmetic or pharmaceutical compositions; it also concerns the use of lysine pidolate or arginine pidolate combined with at least one phenolic derivative.

It is known that fatty substances tend to oxidize even at ambient temperature, and this oxidation (or tendency to become rancid) causes them to acquire new properties, in particular gustatory or olfactory properties which are normally considered to be undesirable when these fatty substances are incorporated, for example, into food or cosmetic mixtures.

To prevent oxidation, the fatty substance-based compositions formed contain protective, or antioxidant agents.

Conventional antioxidants include, in particular, ascorbic acid, which works mainly by direct absorption of oxygen. However, ascorbic acid has the disadvantage of having a low solubility in fatty substances.

To overcome this problem associated with ascorbic acid, the use of various ascorbyl esters, such as ascorbyl stearate, palmitate, or laurate, for example, has also been suggested, Furthermore, it is known that, in addition to their own antioxidant properties, the ascorbic derivatives also improve the activity of antioxidants such as tocopherols or caffeic acid and its esters, by promoting the regeneration of these antioxidants.

Proposals have also been made for various improvements in these binary antioxidants of the type associating ascorbic derivatives+tocopherols or ascorbic derivatives+caffeic derivatives, by providing for the addition of a third constituent which further improves the antioxidant effects. The third constituents of these ternary systems include p-aminobenzoic acids, phospholipids, or amines.

It is known, moreover, that some amino acids possess antioxidant properties Ahmad, M. M., JAOCS, 60(4), 1983, pp. 837-840. The antioxidant properties of these amino acids can, in particular, be strengthened through combination with various other antioxidant substances, such as α-tocopherol, for example.

Following various studies, it has now been found that excellent antioxidant activity could be obtained in cosmetic mixtures, by using lysine pidolate or arginine pidolate as the active ingredient.

Lysine pidolate and arginine pidolate have been mentioned in the literature as hydrating agents; however, they have never been described as having antioxidant properties.

Thus, the present invention concerns the use of lysine pidolate or arginine pidolate as an antioxidant in the preparation of a cosmetic or pharmaceutical composition designed for treating the skin, and in particular for treating aging skin.

Arginine pidolate and lysine pidolate are, as indicated above, conventional products which have been described by Zanotti, PRODOTTO CHIMICO, Marzo 1982, pp. 25-28.

According to the invention, arginine and/or lysine pidolate is used in cosmetic compositions in a concentration of between 0.1 and 20% by weight, and preferably between 1.5 and 10% by weight.

According to a special embodiment of the invention, a synergistic effect produced by the antioxidant action is obtained by combining arginine pidolate and/or lysine pidolate with at least one phenolic derivative.

According to the invention, the phenolic derivatives include the group of phenolic or polyphenolic compounds corresponding to the following functional definition:

At a concentration of between 0.1 and 0.2%, the phenolic derivative placed in the presence of 0.6% ascorbyl palmitate forms a mixture to which vitamin F is added and which, when subjected to the Rancimat test at 100° C. under a current of air at 20 ml/h, has a time of resistance to oxidation of at least 200 minutes, ±10 minutes.

The phenolic derivatives corresponding to this definition include tocopherol or one of its derivatives, butylhydroxytoluene or one of its derivatives, such as benzylidene camphor butylhydroxytoluene, and the esters or amides of caffeic acid.

The term "tocopherol" signifies not only α-tocopherol, but also β, γ-, or δ-tocopherol and mixtures of them. Tocopherol derivatives include precursors of tocopherol, in particular esters of tocopherol such as tocopherol acetate and tocopherol nicotinate.

Esters of caffeic acid include, in particular, alkyl esters such as methyl, ethyl, or butyl esters and phytol ester. Among the amides of caffeic acid, mention may be made of N-alkylamides, such as N-octyl amide.

As will be reported below, the studies conducted have made it possible to reveal an important synergistic effect when the arginine pidolate or lysine pidolate was combined with a phenolic derivative, especially with tocopherol.

According to this embodiment of the invention, the phenolic derivative was generally present in a concentration of between 0.005 and 5% by weight, and preferably between 0.1 and 2% by weight.

The concentration of lysine pidolate and/or arginine pidolate normally ranged between 0.1 and 20% of the total weight of the composition.

Antioxidant efficacy was demonstrated using the method for accelerated oxidation of vitamin F, which is a substance particularly sensitive to oxidation.

An automatic Rancimat apparatus marketed by the Metrohm company was used for this study (A. Seher et al., Fette, Seifen, Anstrichmittel 88(1) 1-6, 1986).

Mixtures were prepared in vitamin F using various quantities of tocopherol alone, lysine pidolate, and arginine pidolate, as well as binary systems of a tocopherol and of a lysine pidolate, on the one hand, and of a tocopherol and of an arginine pidolate, on the other. These binary mixtures were studied in different concentrations.

Each sample was heated to 100° C. and subjected to air bubbling (20 liters/h). The concentration of the volatile acids resulting from the decay of the hydroperoxides and of the aldehydes of vitamin F was continuously monitored in a cell filled with water, in which a platinum electrode was immersed. This electrodes measured, as a function of time, the increase in conductivity caused by the increase of the concentration of volatile acids. The induction time was determined by the intersection of the two asymptotes of the exponential oxidation curve obtained.

This time corresponds to the latency time preceding the auto-oxidation of the vitamin F. The longer the latency time, the greater the resistance of the vitamin F to auto-oxidation.

The results obtained are brought together in the following table.

| Tocopherol | Lysine Pidolate | Arginine Pidolate | Induction Time in mn |
|---|---|---|---|
| 0.1% | — | — | 42 |
| — | 0.75% (2.6 m.mole) | — | 126 |
| — | — | 0.83% (2.7 m.mole) | 54 |
| 0.1% | 0.75% (2.6 m.mole) | — | 963 |
| 0.1% | 1.5% (5.2 m.mole) | — | 1371 |
| 0.1% | — | 0.83% (2.7 m.mole) | 1845 |
| 0.1% | — | 1.66% (5.4 m.mole) | 2844 | m.mole = millimole

These results clearly show that the binary systems exhibit excellent antioxidant activity.

The invention also concerns compositions containing fatty substances, in particular food, cosmetic, or dermatological-pharmaceutical mixtures.

The fatty substances present in the compositions according to the invention are, for example, animal fatty substances such as cetin, beeswax, lanolin, perhydrosqualene, turtle oil, etc.; vegetable fatty substances existing as oils, fats, or waxes, such as sweet almond oil, avocado oil, olive oil, sesame oil, or macadamia oil; hydrogenated coconut or palm oils, cocoa butter, carnauba wax, or montana wax; and synthetic oils formed from esters and/or ethers of glycerol or glycol, such as those, for example, described in French Patents Nos. 75,24656, 75,24657, and 75,24658.

The cosmetic or dermatological-pharmaceutical compositions may contain, in addition to the fatty substances oxidizable to varying degrees, products sensitive to oxidation, such as vitamin F or β-carotene, for example.

The compositions according to the invention exist as oleaginous solutions, water-in-oil or oil-in-water emulsions, possibly anhydrous solid products, lotions or microdispersions, and vesicular dispersions. The lipids forming the vesicles can be of the ionic or non-ionic type, or a mixture of these latter. They are also used to make skin-care lotions, creams (creams for the face, hands, and body, sun-screen creams, make-up remover creams, foundation creams), liquid foundations, make-up remover lotions, sun-screen lotions, bath oils, lipsticks, eye liners, deodorant sticks, etc.

For topical application, the pharmaceutical compositions according to the invention contain the vehicles and ingredients required to enable the composition to exist in the form of ointments, creams, lotions, pomades, and oily solutions.

According to a preferred embodiment, the cosmetic or dermatological-pharmaceutical compositions exist in a form designed to be applied topically, in particular as creams intended to protect against oxidation of the lipids of the skin.

In the compositions according to the invention, the antioxidant as specified above is normally present so as to give the following proportion in relation to the total weight of the composition:

Arginine or lysine pidolate ................. 0.1 to 20%
Phenolic derivative ......................... 0.005 to 5%

The compositions according to the invention can, moreover, contain active compounds or ingredients used conventionally in the aforementioned compositions, such as surfactants, coloring agents, perfumes, astringents, ultraviolet-absorbing products, and organic solvents. These compositions are prepared using conventional techniques.

Several examples of the compositions according to the invention are given below.

| EXAMPLE 1: Hydrating Cream | |
|---|---|
| Lysine pidolate | 5.0% |
| Mg lanolate | 3.0% |
| Alcohol of lanolin | 5.0% |
| Vaseline oil | 27.0% |
| Vaseline | 15.0% |
| Methyl parahydroxybenzoate | 0.2% |
| Propyl parahydroxybenzoate | 0.1% |
| Demineralized water qsp | 100.0% |
| EXAMPLE 2: Day Protective Cream | |
| Arginine pidolate | 10.0% |
| Auto-emulsifiable glycerol stearate | 3.0% |
| Cetyl alcohol | 0.5% |
| Stearyl alcohol | 0.5% |
| Vaseline oil | 12.0% |
| Sesame oil | 10.0% |
| Stearic acid | 3% |
| Methyl parahydroxybenzoate | 0.2% |
| Propyl parahydroxybenzoate | 0.1% |
| Perfume | 0.3% |
| Demineralized water | 100 |
| EXAMPLE 3: Hydrating Protective Cream | |
| Lysine pidolate | 10% |
| Tocopherols | 1.0% |
| Vitamin E acetate | 1.0% |
| Glycerol stearate | 3.0% |
| Stearyl alcohol | 0.5% |
| Stearic acid | 2.0% |
| Perhydrosqualene | 12.0% |
| Volatile silicone oil | 5.0% |
| Methyl parahydroxybenzoate | 0.2% |
| Propyl parahydroxybenzoate | 0.1% |
| Perfume | 0.3% |
| Demineralized water | 100.0% |
| EXAMPLE 4: Protective Hand Cream | |
| Arginine pidolate | 1.5% |
| Methyl caffeate | 0.4% |
| Tween 60 (sorbitan monostearate polyoxyethylenated with 20 moles ethylene oxide) | 2.0 |
| Cetyl alcohol | 1.0 |
| Isopropyl myristate | 3.0 |
| Vaseline oil | 7.0 |
| Volatile silicone oil | 7.0% |
| Methyl parahydroxybenzoate | 0.2% |
| Propyl parahydroxybenzoate | 0.1% |
| Demineralized water qsp | 100.0% |
| EXAMPLE 5: Vesicular Diersion | |
| Lysine pidolate | 1.0% |
| α-tocopherol | 0.05% |
| Hydrogenated soy lecithin | 1.8% |
| Cholesterol | 0.9% |
| Collagenous lipacide palmitoyl | 0.3% |
| Glycerine | 3.0% |
| Macadamia oil | 15.0% |
| Volatile silicone oil | 10.0% |
| Carboxyvinyl polymer sold under the name "CARBOPOL 940" by the Goodrich company | 0.6% |
| Methyl parahydroxybenzoate | 0.2% |
| Triethanolamine       qs pH = | 6 |
| Demineralized water qsp | 100.0 |

We claim:

1. A method of inhibiting oxidation in a cosmetic or pharmaceutical composition intended for the treatment of the skin comprising combining with the cosmetic or pharmaceutical vehicle of said composition an anti-oxidant mixture comprising:
   (i) from 0.1 to 20% by weight of an active ingredient selected from the group consisting of lysine pidolate, arginine pidolate and mixtures thereof, and
   (ii) from 0.005 to 5% by weight of a phenolic derivative selected from the group consisting of tocopherol and derivatives thereof, butylhydroxytoluene and derivatives thereof, and esters and amides of caffeic acid.

2. The method of claim 1 wherein the derivative of butylhydroxytoluene is benzylidene camphor butylhydroxytoluene.

3. The method of claim 1 wherein the tocopherol is selected from $\alpha$-tocopherol, $\beta$-tocopherol, $\gamma$-tocopherol, $\delta$-tocopherol and mixtures thereof.

4. The method of claim 1 wherein the tocopherol derivatives are selected from the group consisting of tocopherol acetate and tocopherol nicotinate.

5. A cosmetic or pharmaceutical composition containing a cosmetically or pharmaceutically acceptable vehicle having an antioxidant mixture having the following proportions in relation to the total weight of said composition:
   (i) from 0.1 to 20% by weight of an active ingredient selected from the group consisting of lysine pidolate, arginine pidolate and mixtures thereof, and
   (ii) from 0.005 to 5% by weight of a phenolic derivative selected from the group consisting of tocopherol and derivatives thereof, butylhydroxytoluene and derivatives thereof, and esters and amides of caffeic acid.

6. The cosmetic or pharmaceutical composition of claim 5 wherein the derivative of butylhydroxytoluene is benzylidene camphor butylhydroxytoluene.

7. The cosmetic or pharmaceutical composition of claim 5, wherein the tocopherol is selected from $\alpha$-tocopherol, $\beta$-tocopherol, $\gamma$-tocopherol, $\delta$-tocopherol and mixtures thereof.

8. The cosmetic or pharmaceutical composition of claim 5 wherein the tocopherol derivatives are selected from the group consisting of tocopherol acetate and tocopherol nicotinate.

* * * * *